(12) United States Patent
Crompton et al.

(10) Patent No.: US 10,672,520 B1
(45) Date of Patent: Jun. 2, 2020

(54) PRECISION MEDICINE APPROACH TO IMPROVING PATIENT SAFETY AND ACCESS TO MRI

(71) Applicant: AltaSim Technologies, LLC, Columbus, OH (US)

(72) Inventors: Jeffrey Crompton, Columbus, OH (US); Kyle Koppenhoefer, Columbus, OH (US); Orlando Simonetti, Columbus, OH (US); David Gross, Westerville, OH (US)

(*) Notice: Subject to any disclaimer, the term of this patent is extended or adjusted under 35 U.S.C. 154(b) by 0 days.

(21) Appl. No.: 15/448,575

(22) Filed: Mar. 2, 2017

Related U.S. Application Data

(60) Provisional application No. 62/302,443, filed on Mar. 2, 2016.

(51) Int. Cl.
| | |
|---|---|
| *G16H 50/50* | (2018.01) |
| *A61B 6/03* | (2006.01) |
| *A61B 6/12* | (2006.01) |
| *A61B 5/01* | (2006.01) |
| *A61B 5/055* | (2006.01) |

(52) U.S. Cl.
CPC .......... *G16H 50/50* (2018.01); *A61B 5/015* (2013.01); *A61B 5/055* (2013.01); *A61B 6/032* (2013.01); *A61B 6/12* (2013.01)

(58) Field of Classification Search
CPC ........ A61N 1/372; A61B 5/055; A61B 5/686; A61B 2017/005; A61B 5/01; A61B 5/015; A61B 6/032; A61B 6/12; A61B 2090/374; A61B 2018/00791; A61B 2090/3954; A61B 5/076; G16H 50/50; G06F 19/3437

See application file for complete search history.

(56) References Cited

U.S. PATENT DOCUMENTS

| | | | | |
|---|---|---|---|---|
| 9,268,003 B2* | 2/2016 | Griffin | ................... | G01R 33/48 |
| 9,415,213 B2* | 8/2016 | Venook | ................... | A61N 1/08 |
| 9,874,620 B2* | 1/2018 | Ahmad | ................... | G01R 33/48 |
| 2003/0163177 A1* | 8/2003 | Eggers | ................... | A61B 18/04 |
| | | | | 607/96 |
| 2003/0225331 A1* | 12/2003 | Diederich | ............... | A61N 7/02 |
| | | | | 600/437 |
| 2004/0009459 A1* | 1/2004 | Anderson | ........... | G06F 19/3481 |
| | | | | 434/262 |

(Continued)

*Primary Examiner* — Jingge Wu
(74) *Attorney, Agent, or Firm* — Lorraine Hernandez; Kegler, Brown, Hill + Ritter Co., LPA

(57) ABSTRACT

Disclosed is a method for determining, among other things, the temperature profile of a medical implant in a patient when subjected to an MRI scan or machine, thus enabling a determination of the risk of temperature induced tissue necrosis or damage to the implant. The specific position of the implant in the patient changes the temperature dispersion in the body and is accounted for in the creation of the temperature profile. The method includes mapping with an imaging unit location, size and orientation of the medical implant in a patient, and storing the location, size and orientation in a mapped data. Then, translating the data to a model patient of gender, age, weight, height, and body structure of the patient with a model medical implant. Further, determining the parameters of an MRI unit to be used and computing the temperature profile of the implant to ascertain temperature impact.

10 Claims, 8 Drawing Sheets

(56) References Cited

U.S. PATENT DOCUMENTS

| | | | | |
|---|---|---|---|---|
| 2005/0015128 | A1* | 1/2005 | Rezai | A61N 1/0529 607/115 |
| 2005/0065501 | A1* | 3/2005 | Wallace | A61B 17/12022 606/1 |
| 2008/0208276 | A1* | 8/2008 | Wedan | A61N 1/3718 607/27 |
| 2008/0228092 | A1* | 9/2008 | Wedan | A61B 5/7225 600/509 |
| 2009/0221902 | A1* | 9/2009 | Myhr | A61M 37/0092 600/411 |
| 2010/0036466 | A1* | 2/2010 | Min | A61N 1/05 607/116 |
| 2010/0121179 | A1* | 5/2010 | Min | G01R 33/583 600/421 |
| 2011/0066028 | A1* | 3/2011 | Min | A61B 5/01 600/412 |
| 2011/0190860 | A1* | 8/2011 | Harberts | A61N 1/0534 607/116 |
| 2013/0035921 | A1* | 2/2013 | Rodriguez-Ponce | A61B 5/015 703/11 |
| 2013/0261368 | A1* | 10/2013 | Schwartz | A61N 5/1027 600/1 |
| 2014/0067030 | A1* | 3/2014 | Walker | A61N 1/056 607/116 |
| 2014/0210472 | A1* | 7/2014 | Homann | G01R 33/36 324/309 |
| 2014/0249612 | A1* | 9/2014 | Bonmassar | C09K 19/3809 607/116 |
| 2015/0015254 | A1* | 1/2015 | Zhu | A61B 5/055 324/309 |
| 2015/0018667 | A1* | 1/2015 | Radman | A61N 1/20 600/411 |
| 2015/0242588 | A1* | 8/2015 | Audigier | G06F 19/3437 606/41 |
| 2016/0077169 | A1* | 3/2016 | Cohen | G01R 33/288 324/311 |
| 2016/0232690 | A1* | 8/2016 | Ahmad | G01R 33/48 |
| 2016/0331960 | A1* | 11/2016 | Katnani | A61N 1/08 |

\* cited by examiner

PRECISION MEDICINE APPROACH TO IMPROVING PATIENT SAFETY AND ACCESS TO MRI

This non-provisional application claims the benefit of U.S. Provisional Application No. 62/302,443, filed on Mar. 2, 2016, which is herein incorporated by reference in its entirety.

BACKGROUND

MRI is a powerful diagnostic imaging modality providing highly detailed images throughout the human body without the use of ionizing radiation and is used to scan more than 30 million patients every year in the United States. Organization for Economic Co-operation and Development (2012). Magnetic resonance imaging (MRI) exams, total. Health: Key Tables from OECD, No. 46.

Each year about 600,000 pacemakers are implanted and in 2002 there were about three (3) million patients worldwide living with implanted pacemakers. Wood M A, Ellenbogen K A. Cardiology patient pages. Cardiac pacemakers from the patient's perspective. Circulation, 2002; 105:2136-2138.

Significantly higher numbers of patients are implanted with other active and passive medical devices. Studies have shown that up to 75% of patients with implanted pacemakers will require Magnetic Resonance Imaging (MRI) within the lifetime of their device. Kalin R, Stanton M S. Current clinical issues for MRI scanning of pacemaker and defibrillator patients. Pacing Clin Electrophysiol 2005; 28:326-8. Significantly higher numbers of patients with other types of implanted medical devices are expected to require MRI.

Exposure of an implanted medical device to the electromagnetic fields generated by an MRI system can damage surrounding tissue, reduce the effectiveness of the device, promote migration of the device, or cause tissue necrosis. For example, one of the safety concerns for patients with any implanted device is RF induced heating during MRI. When electrically conductive materials are subjected to oscillating magnetic fields, electric currents are induced, which cause heating and increase the temperature in the surrounding tissue, potentially reducing the effectiveness of the device or causing tissue necrosis.

Currently, these safety concerns cause more than one million patients with pacemakers, implanted cardioverter defibrillators (ICDs) and other implanted devices to be denied access to MRI procedures on an annual basis worldwide. Martin E T. Can cardiac pacemakers and magnetic resonance imaging systems co-exist? Eur Heart J, 2005; 26(4):325-327. Although a limited number of MRI-conditional devices, such as pacemakers, are becoming available, and previous studies have demonstrated successful 1.5 T MRI procedures for some patients with pacemakers, the vast majority of implanted devices are contraindicated for MRI. MRI-conditional devices represent only a small fraction of the devices in use worldwide, and millions of patients have existing implanted devices that are not registered as safe for exposure to conventional MRI fields. Wood M A, Ellenbogen K A. Cardiology patient pages. Cardiac pacemakers from the patient's perspective. Circulation, 2002; 105:2136-2138. Further, the move towards higher magnetic field strengths (e.g., 3.0 T and 7.0 T) makes MR safety a growing concern.

The Food and Drug Administration (FDA) currently requires medical device manufacturers to evaluate the MR safety of their medical devices. However, the currently accepted standard test method (ASTM F2182) for measuring RF induced heating does not accurately predict in vivo tissue damage or account for physiologic heat transfer mechanisms. Current attempts to extrapolate in vitro behavior to in vivo environments overly simplify the relationship between applied RF energy and device heating to an extent that safe exposure to MRI operation cannot be reliably ascertained. Similarly, tests to measure the effect of the Gradient coil and permanent magnetic field of an MRI machine are not representative of in vivo application, and the collected data cannot be safely extrapolated to humans.

Conventional methods that estimate RF induced heating through correlations with Specific Absorption Rate (SAR) and temperature rise or, when extended for in vivo, apply transfer function approaches that are arbitrary abstractions of the response of real device geometries in real body habitus. Current predictions of SAR are accomplished using Finite Difference Time Domain (FDTD) that has significant inherent restrictions on the accurate representation of the complexity of the geometry and orientation of the implanted device. Thus, these approaches rely on simplifying assumptions that restrict integration of patient and device specific information and thus patient specific precision medicine approaches are not possible with the traditional methodologies.

The current clinical practice paradigm for assessing the MR safety risks of patients with implanted devices is reliant on safety data collected under conditions that misrepresent clinical application. Simplified in vitro safety tests do not account for patient-specific information such as device placement and orientation, the effect of local blood flow in the body, the type of MRI scanner hardware, or MRI electromagnetic fields. These parameters significantly impact the potential for interaction between the MRI's electromagnetic field and the implanted device and thus have to be included in any patient specific risk assessment.

The current test standards used to determine MR safety are overly conservative because they do not represent in vivo physiological conditions, and do not account for patient specific factors such as body habitus and device geometry. As a result, patients with pacemakers, ICD's, and other implanted devices may be inappropriately withheld from critical MRI scans because their devices are considered unsafe. Thus, there is a need for a method to determine the how an implant will react to an MRI scan which overcomes the limitations of the prior art.

SUMMARY OF THE INVENTION

The present invention overcomes limitations by evaluating the effect of MRI fields on an implanted medical device in an individual patient with their specific implanted device.

The present disclosure is the integration of a computational tool that predicts the interaction between an MRI electromagnetic field and an implanted device to predict the effect on surrounding tissue and device functionality with patient and device related information such that the effect of exposure of an implanted device to an MRI electromagnetic for an individual patient can be predicted. The computational tool incorporates factors such as, but not limited to, device type, orientation and materials of construction, MRI system operating procedures, and patient biometric factors into a computational model to predict the influence of electromagnetic fields associated with an MRI on implanted devices under the specific in vivo conditions encountered in an individual patient.

Device location and orientation within the patient, and specific device dimensions (if unknown) can be obtained from x-ray computed tomography or multi-planar radiographs of the patient or other standard medical imaging technologies. Patient may include, for example, age and gender as well as measurements of height, weight, and circumference. Implanted device specifications and material properties may be known, or reasonable assumptions made. MRI system parameters (e.g., field strength, maximum spatial gradient, maximum gradient slew rate) are available from the MRI manufacturer, and specific scan parameters are defined by the clinical indication for MRI. The results of this computational model will provide an assessment of the risk of having an MRI for a patient with a specific implanted device. This will improve patient safety and increase access to critical diagnostic information by use of a personalized, precision healthcare approach.

Also disclosed is a system for improving access to an MRI for patients with implanted medical devices as disclosed herein.

Further disclosed is a method for providing a patient-specific risk assessment of MRI safety due to induced heating, device damage and device migration for patients with implanted medical devices comprising:
 (a) Patient-specific information including gender, body habitus (e.g., height, weight, waist measurements, etc.) and positioning within the bore of the scanner (e.g., head-first supine).
 (b) MRI system information for RF coil operation and MR sequence protocol that will be applied.
 (c) MRI system information for gradient coil operation.
 (d) MRI system information for permanent magnetic field gradient.
 (e) Implanted device specifications (e.g., manufacturer and model).
 (f) Device geometry and orientation in the patient, obtained from radiographs of the patient.
 (g) Physiological cooling mechanisms representative of regular human physiology.

Additionally disclosed is a computational simulation tool that is run on a local computer or a cloud based system, that can predict the interaction of electrically active and/or electrically passive implanted medical devices such as, but not limited to, neurostimulators, pacemakers, pacemaker leads and implanted cardioverter defibrillators (ICD's), stents, orthopedic implants, etc. with electromagnetic fields, such as the radio frequency (RF) electromagnetic radiation and magnetic gradients, used in Magnetic Resonance Imaging (MRI).

BRIEF DESCRIPTION OF THE DRAWINGS

Aspects of the disclosure are understood from the following description when read with the inline drawings. Elements, structures, etc. of the drawings may not necessarily be drawn to scale. Accordingly, the dimensions of the same may be arbitrarily increased or reduced for clarity of discussion.

DETAILED DESCRIPTION OF THE DRAWINGS

Figure 1:
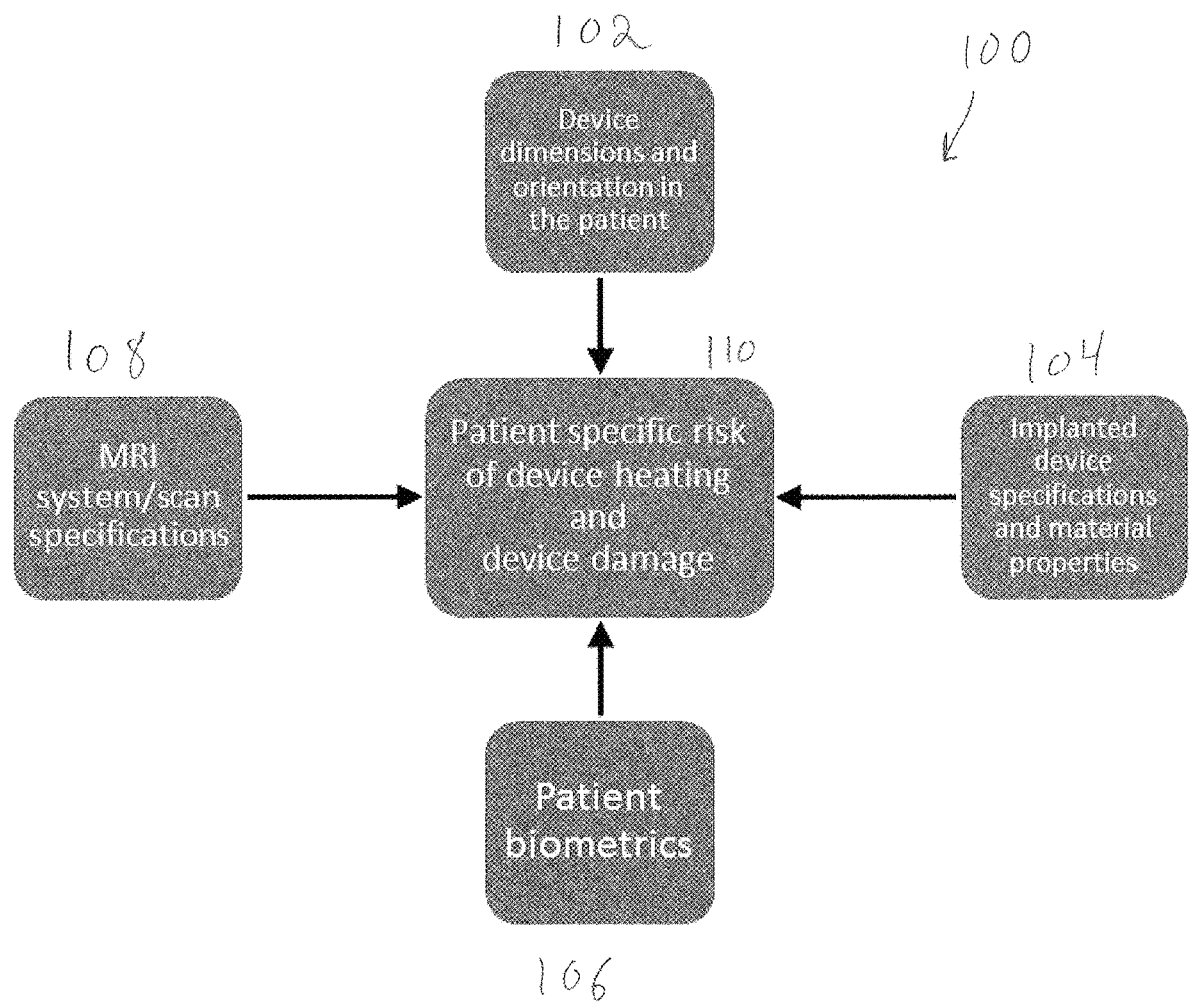
FIG. 1 illustrates a flowchart of a method to determine patient specific risk of device heating due to an MRI machine.

The presently disclosed method identifies risks associated with an MRI scanner and its interaction with embedded medical devices in a patient. In particular, devices implanted within a body may undergo rapid heating when a magnetic field from an MRI scanner is applied to the patient. As the device heats up, it may exceed a safe temperature threshold which would induce damage and tissue necrosis in the patient.

Calculating the increase of temperature in the device prior to subjecting the patient to an MRI scanner allows a physician to properly evaluate the risks of tissue damage against the need for an MRI scan. The more accurate the simulation, the more informed and accurate the decision making process with be for the physician. Simulations which are not as accurate as the disclosed method will make certain assumptions during their calculations, showing a temperature increase which is purposefully designed to be higher than reality. This is done as a safety measure, but prevents many patients from getting access to an MRI scanner.

There are a large number of factors which, if taken, improve the accuracy of the simulation. Said factors may include, for example, the blood flow in the patient. The blood flow will help cool the device as the blood moves around the body, much in the same way as a water radiator. Further, tattoos and other unique objects in a patients' body can change the temperature calculation. The currently disclosed method may take in consideration some or all of these factors, improving the accuracy over the prior art.

Implanted devices that may be affected during MRI include, but are not limited to, passive implanted devices such as stents and orthopedic implants, and active implants such as pacemakers, pacemaker leads, implanted cardioverter defibrillators (ICD's), and neuro-stimulators. The extent to which the device is affected during MRI exposure is dependent on a number of factors including, but not limited to, technical specifications of the device, device size, orientation and geometric configuration; device positioning with respect to organs and tissues within the body; inherent physiological cooling mechanisms such as blood flow and tissue perfusion; patient body habitus and position within the MRI scanner; MRI scanner specifications and scan parameters.

The precise location of the medical device within the patient's body is also important. For example, stints or other wire like apparatuses may extend throughout the body in different ways and locations. The heating on the stint caused by an MRI machine will then be non-uniform.

The positioning of the patient within the MRI machine is also important, as the magnetic field within the MRI scanner will vary with position. Further, the specific kind of MRI scanner will create different intensities and localized changes within the magnetic field.

The presently disclosed method employs computational analysis methodologies to solve the coupled electromagnetics and transient bioheat transfer, and integrates this with patient specific information to provide a patient-specific risk assessment of MRI electromagnetic field exposure for patients with implanted medical devices. Real device geometry and orientation can be imported into virtual representations of human anatomy, including patient positioning within the bore of the scanner, and then the MRI operating sequences may be invoked. The disclosed method may use scans of human subjects to obtain patient-specific device orientation and patient-specific body habitus. The method may be ran on a local computer or incorporated into a cloud based computation system, enabling users to perform complex computational analysis remotely using secure data transmission.

The integration of patient specific information such as, but not restricted to, device orientation, body habitus and a patient's body type allows a personalized, precision healthcare approach for patient-specific assessments of MR safety. MRI Medical Directors or MRI Safety Officers may use the disclosed method prior to MRI procedures to help assess the risks and benefits of MRI for an individual patient with a specific implanted medical device, configuration within the body and patient body type, and identify safe MRI operating procedures for a specific patient with a specific implanted device. Ultimately, the disclosed method improves patient safety, develop patient specific healthcare protocols and ensure access to critical treatment for patients with implanted devices.

The presently disclosed method may use imaging technology to determine the precise location of a medical device. In an exemplary embodiment, the imaging technology does not subject the patient to significant magnetic fields (e.g., X-ray scanning).

FIG. 1 illustrates a flow chart 100 of an embodiment of the presently disclosed method. There are four factors general which are processed in step 110 to provide Patient specific risk analysis of device heating and damage. The device's specifications and material properties 104, the device's physical dimensions and positioning 102, the specifications of the MRI system 108, and the patient's biometrics 106.

Figure 2:
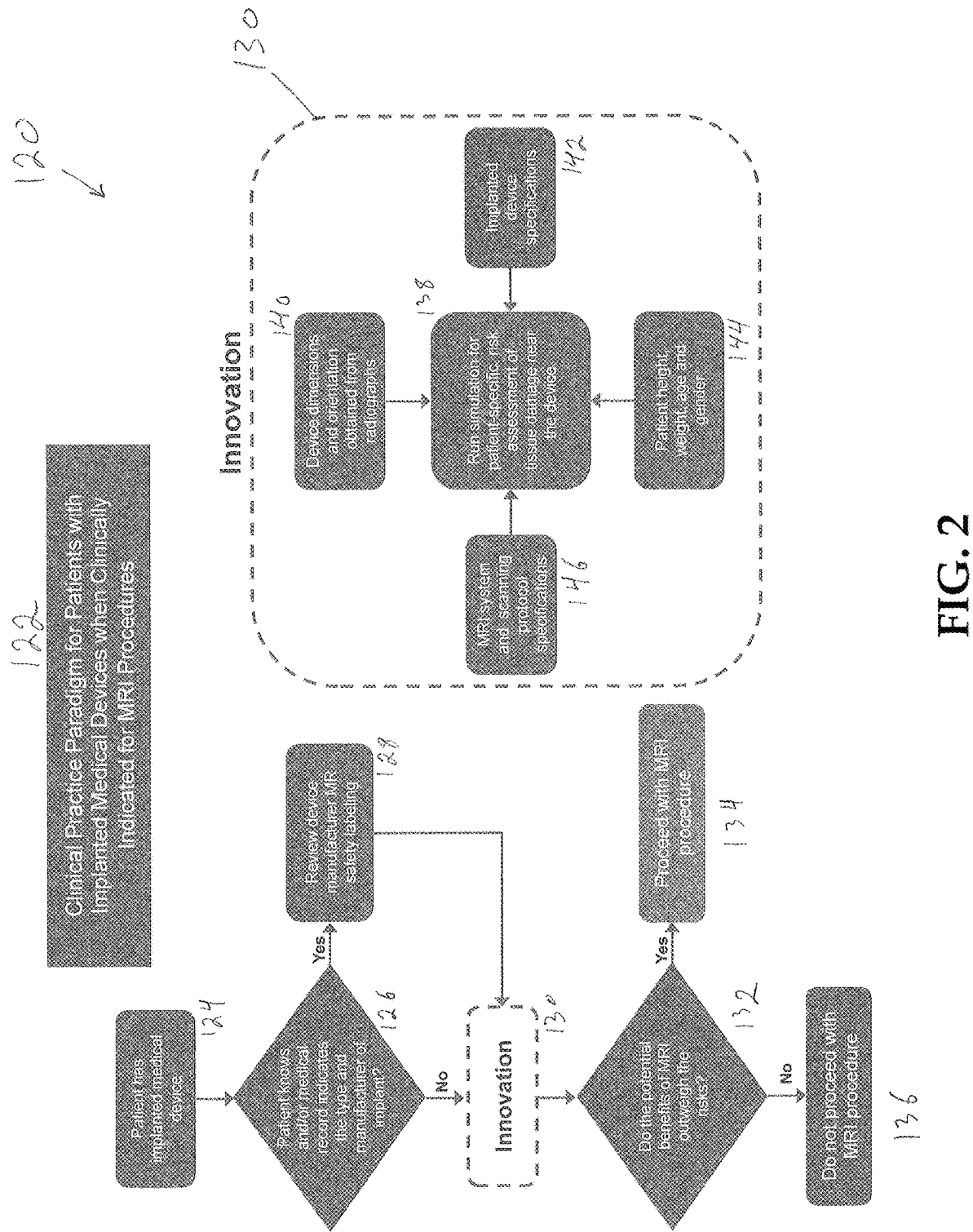
FIG. 2 illustrates a flowchart of a method to determine patient specific risk of device heating due to an MRI machine.

FIG. 2 illustrates a flow chart 120 for how the presently disclosed method for determining risk 130 fits into clinical practice 122. First, a patient has an implanted medical device 124, at which point the determination must be made at step 126 if the implant has specifications which can be used. If so, then those specifications are copied and noted in step 128, which may indicate that the device can be operated in an MRI. Otherwise, the present method 130 can be employed. The goal is to run a simulation 138 for patient specific risk assessment regarding tissue and/or device damage due to temperature increase or displacement of the device. Step 138 is calculated by combing the patient height, weight, age and gender 144, the specifications 142, the device dimension and orientation 140, and the MRI system and scanning protocol specifications 146.

After step 138 is performed, step 130 is complete and a physician may make an assessment 132 if the benefits of the MRI outweigh the risks. If so, the MRI occurs 134. If not, no MRI is performed 136.

Often, the specifications and/or precise location of the implanted medical device are unavailable. In order to determine the position, location, and rotation of the medical device within the patient, multiple non-MRI scans may be taken of the patient. For example, X-ray could be used to scan the patient from a variety of multiple angles. In other embodiments, a CT scan may be performed. Any imaging unit which creates less of a magnetic field than an MRI machine is suitable, although some embodiments may employ any image unit. By combining the multiple angles, the exact position of the device within the patient can be ascertained. In other words, the position of the medical implant is mapped with an imaging machine, and the location, size, and orientation of the device is stored in mapped data.

That mapped data is then used to position a simulated version of the device into a model patient. The data translates the real world position to a simulated model medical implant. The model patient is a virtual and anatomically correct version of a human. The model patient is chosen to have the same biometric markers as the patient (e.g., gender, age, weight, height, body structure).

The parameters of the MRI unite to be used with patient as also ascertained, either from a manufacturer's specification or measurement. In some embodiments, the specifications may approximate the attributes of the MRI machine to be used.

All of the known variable and information is then used to compute the temperature profile of the medical implant upon exposure of the model to the selected MRI procedure, including how that temperature is affected by tissue and blood flow. This temperature profile can then be used to ascertain likelihood of tissue and/or device damage.

In some embodiments, the specific absorption rate may be used during the calculation of the temperature profile. In other embodiments, the medical implant may be a tattoo.

Aspects of the disclosed methods may integrate recent advances in four critical areas to provide a unique and innovative offering.

First, advances in computational analysis to simulate the interaction of electromagnetic fields with implanted devices allow for direct computation of device response due to electromagnetic exposure. These advances are driven by formulations that accurately represent the electromagnetic interactions. This allows for computation of the transient bioheat transfer on and/or near real device geometries that are exposed to electromagnetic fields.

Second, the ability to provide the computational calculations in an easy to use format for routine use has only recently been developed and is a key aspect of this tool for the MRI safety evaluation community.

Third, representations of human body structure in computational analysis files based on scans of human subjects have been improved and permit the use of representative human body structures, or in the extreme allow a representation of the individual patient's body to be included.

Fourth, developments in cloud based high performance computing enable users to perform complex computational analysis remotely using secure data transmission that provide a mechanism for rapid adoption in a global network.

The presently disclosed method will benefit the estimated one million patients who are currently denied access to critical MRI imaging every year due to safety concerns about compatibility with their implanted active devices such as, but not limited to, pacemakers, pacemaker leads and ICDs. The disclosed method may also apply to patients with other active and passive implanted devices that are currently deemed not compatible with MRI exposure such as, but not restricted to, neurostimulators, stents, orthopedic devices. With an ageing population with extended life expectancy and the growing population density requiring implanted devices, the number of patients denied access to critical diagnostic information will continue to increase.

Figure 3A:
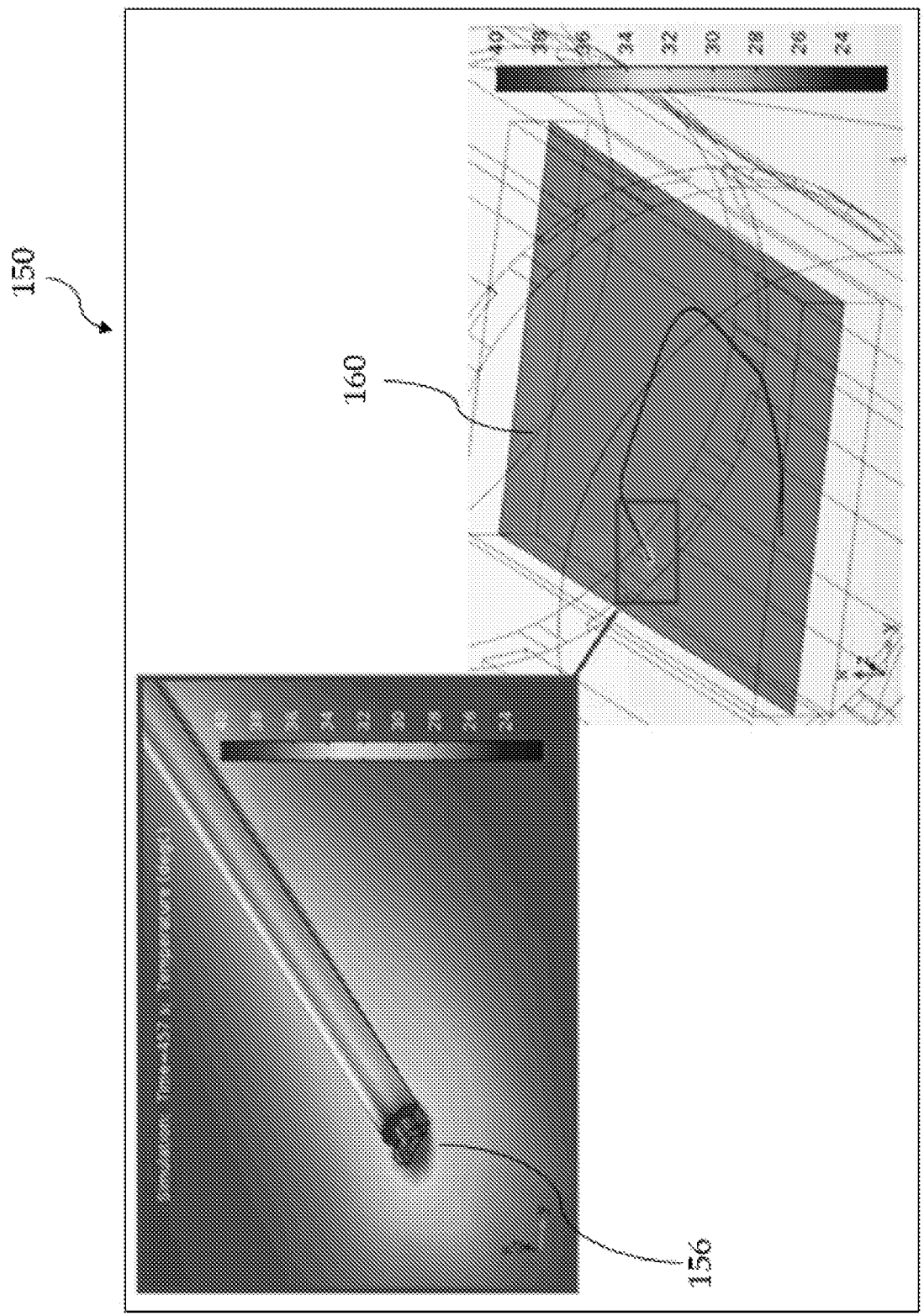
FIG. 3A illustrates a simulation of heating in a medical device undergoing a scan from an MRI machine.
Figure 3B:
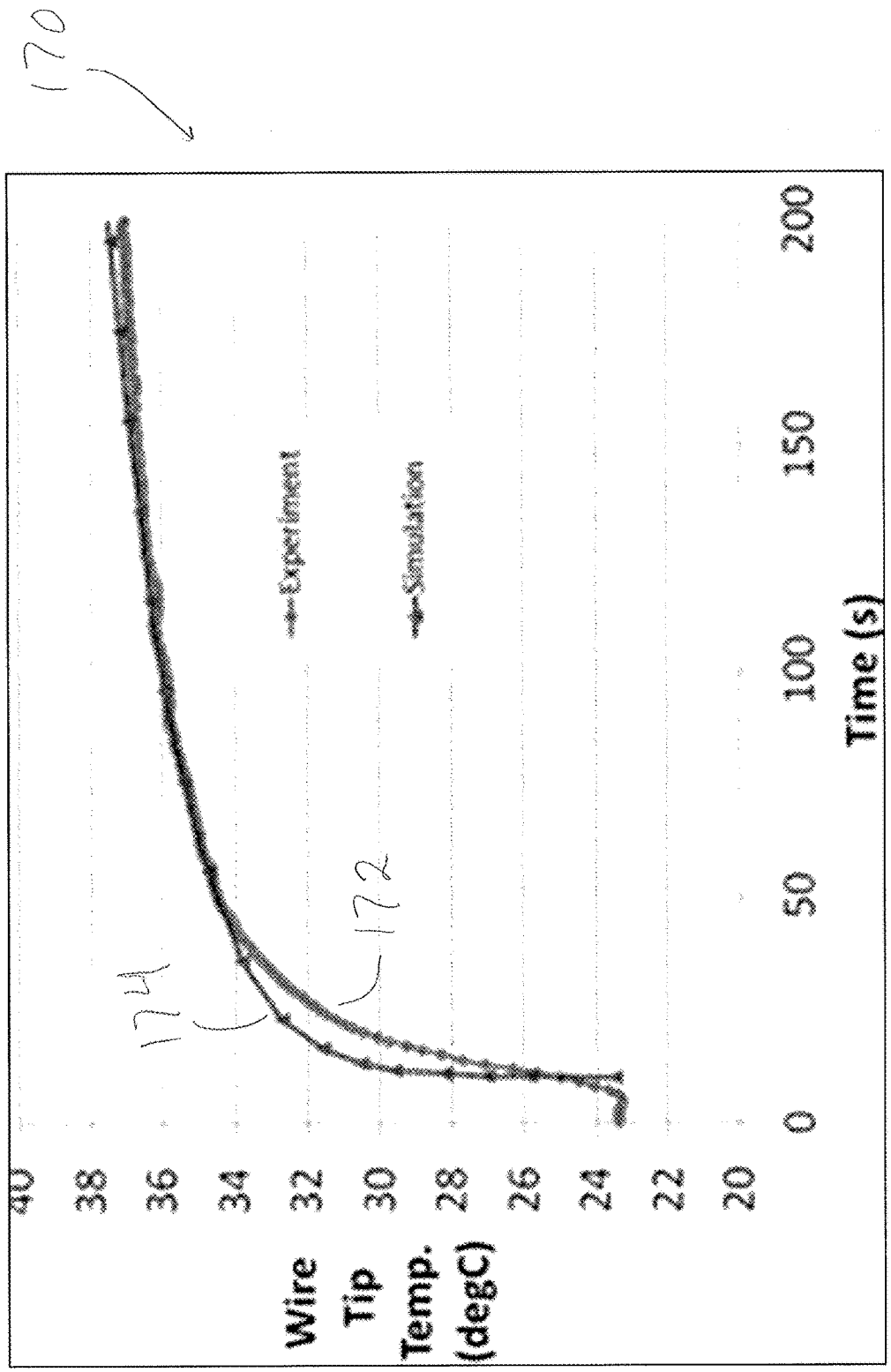
FIG. 3B illustrates a graph of temperature over time of the medical device in FIG. 3A.

One embodiment of the disclosed method has been demonstrated to predict the transient temperature rise associated with electrically passive implanted medical devices (e.g., vena cava filters, stents, abandoned pacemaker leads) when exposed to RF scanning from 1.5 T and 3.0 T MRI systems [5]. A simulated environment 150 of a pacemaker lead wire 156 is illustrated in FIG. 3A. A pacemaker lead wire 156 undergoes a magnetic field from an MRI machine, while suspended in a gel 160. Experimental temperature measurements were made in medical devices exposed to the RF MRI field [6]. FIG. 3B shows a predicted temperature contour 170 of a pacemaker lead wire 156 after 7.5 minutes of RF induced heating during MRI simulation and the measured (172) and predicted (174) transient temperature response during RF exposure. An X-ray computed tomography scan was first acquired to define the geometry of the lead wire embedded in the gel phantom. Accurate transient temperature predictions and the simulated temperature contour of the pacemaker lead wire matched the experimental temperature measurements after 7.5 minutes of RF induced heating in the MR environment. Since the electrode-tissue impedance changes are a function of time at temperature a non-linear response occurs during RF exposure allowing accurate representation of the effect of heating on tissue necrosis. This demonstration of the disclosed method provides a simple example of its ability to incorporate information regarding device geometry, MRI system specifications, and MRI pulse sequence parameters, to predict RF induced heating. More complex embodiments of the invention incorporating additional device characteristics as well as anatomical geometries and realistic physiological cooling mechanisms enable the accurate prediction of transient temperatures for a broad range of devices under a variety of physiological conditions, body locations and body types.

Figure 4A:
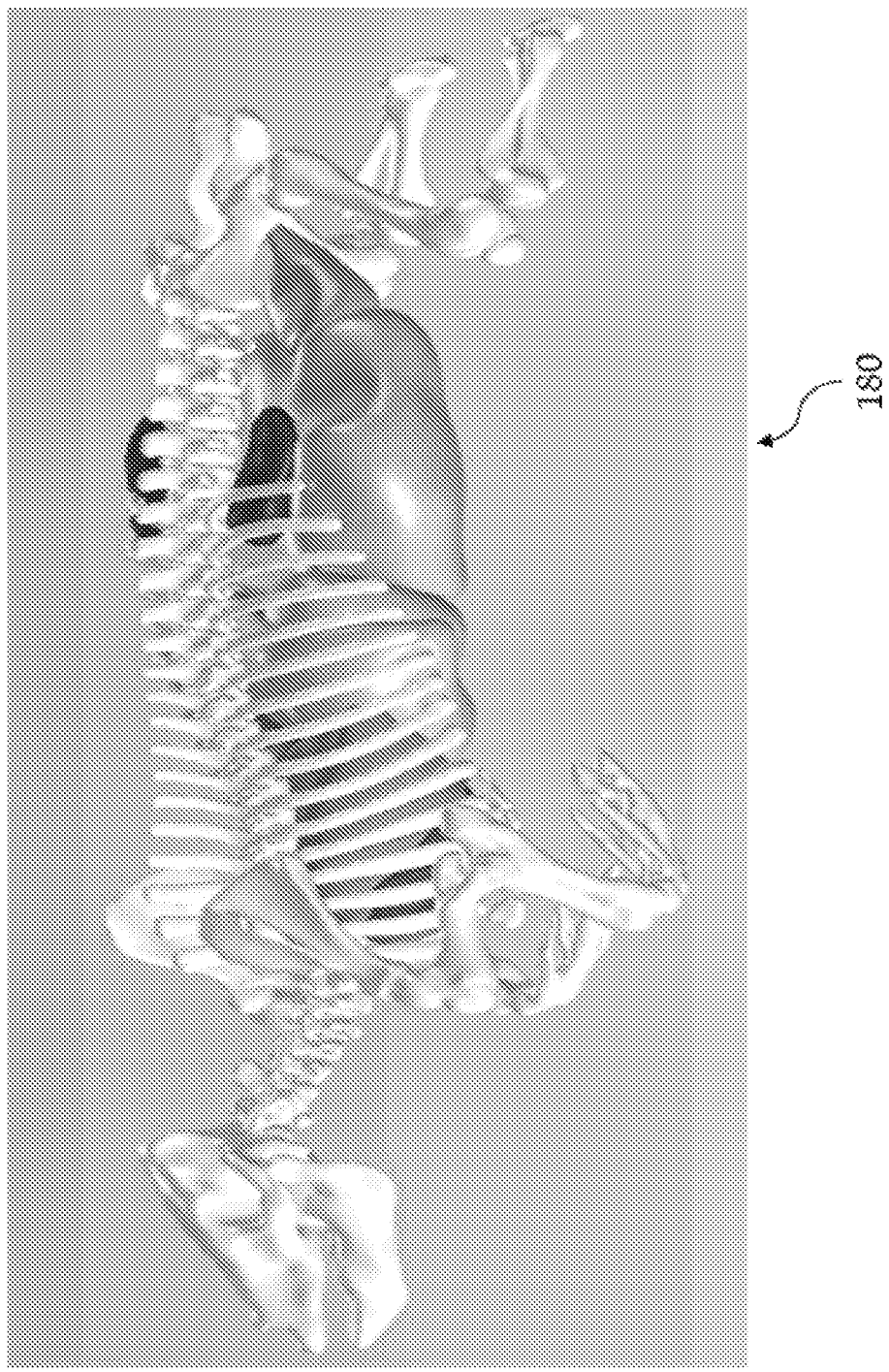
FIG. 4A illustrates the interior of a model pig for simulation purposes.
Figure 4B:
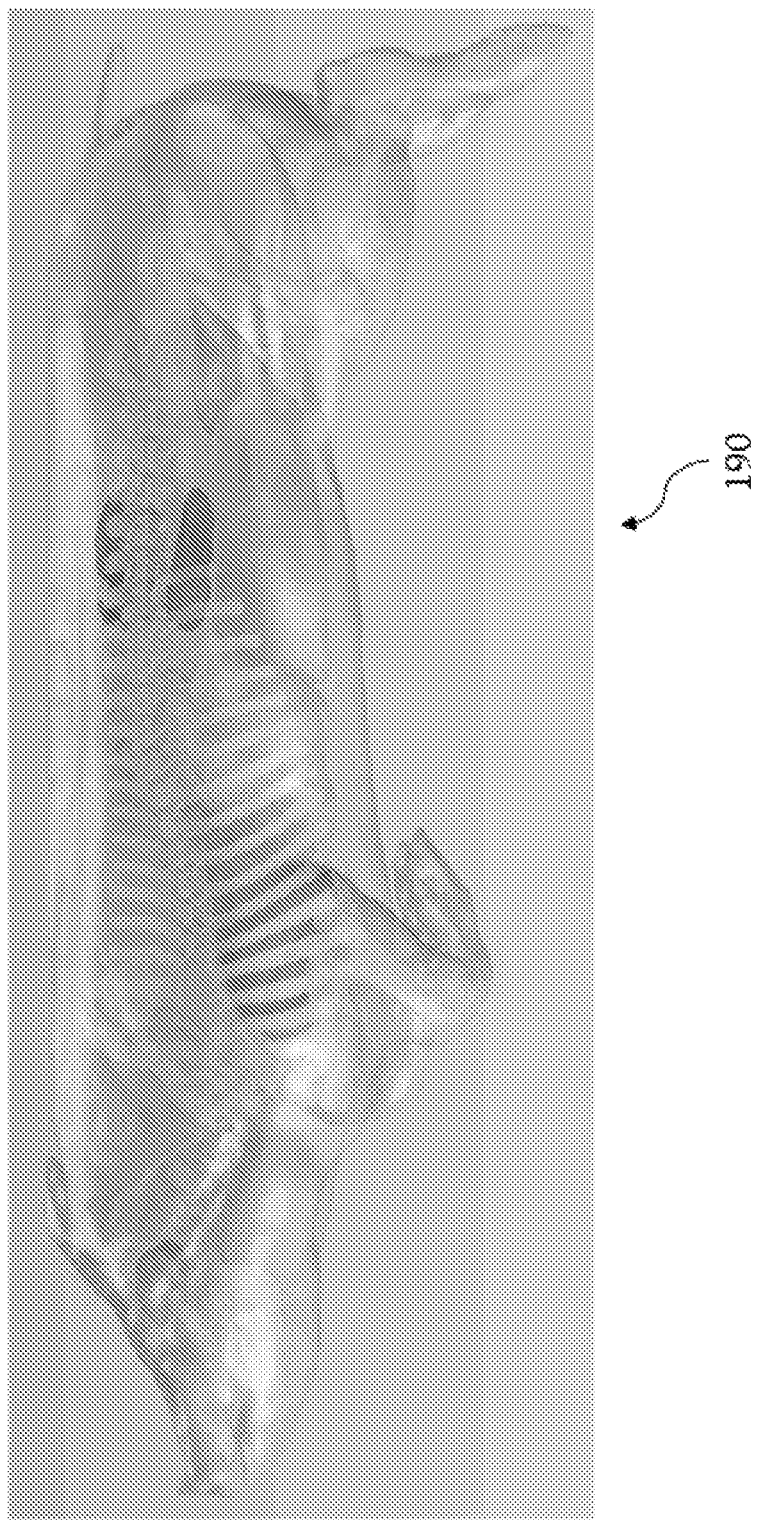
FIG. 4B illustrates a transparent side view of a model pig for simulation purposes.
Figure 5A:
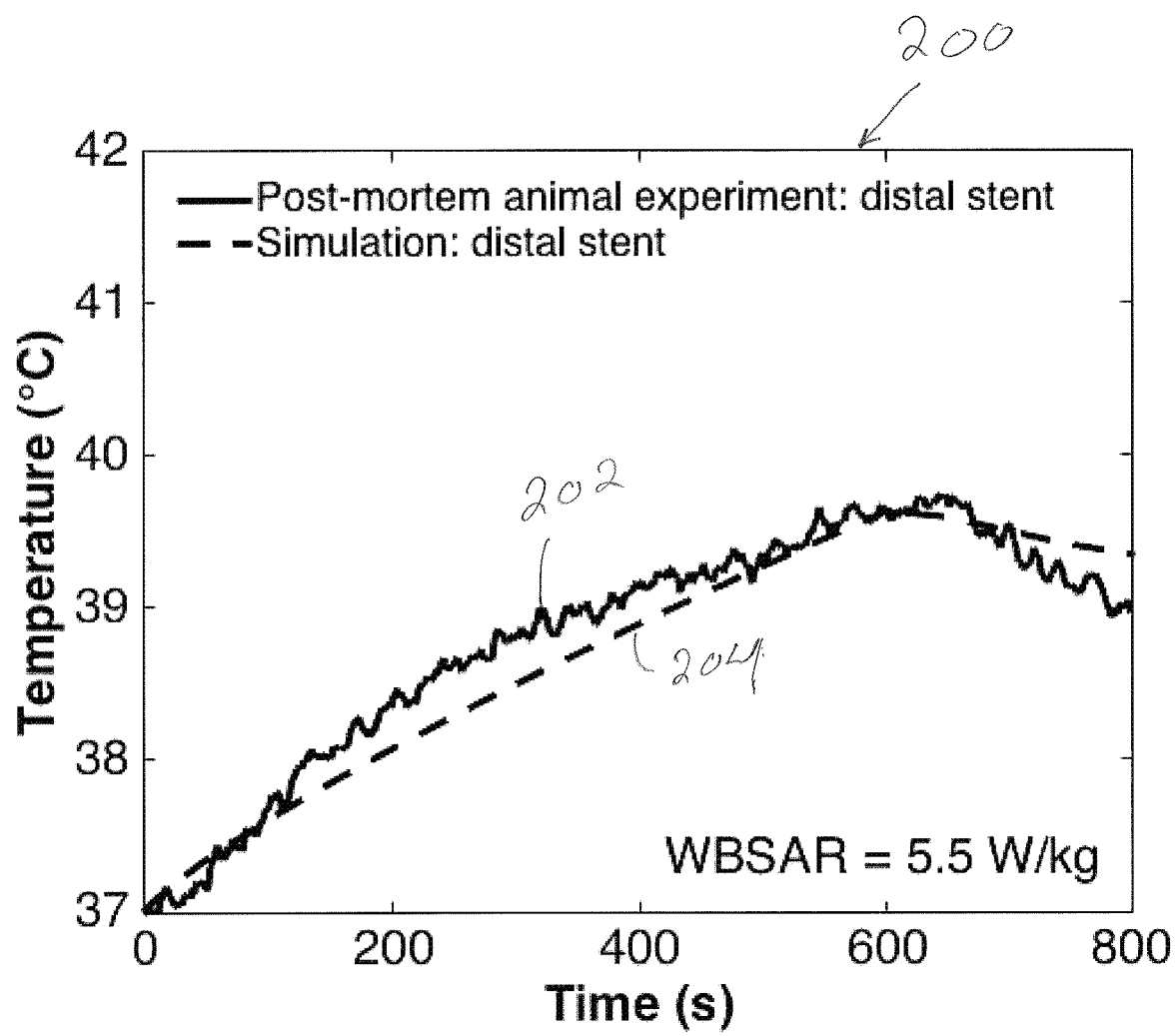
FIG. 5A illustrates a graph of the temperature over time of a distal stent placed into an animal.
Figure 5B:
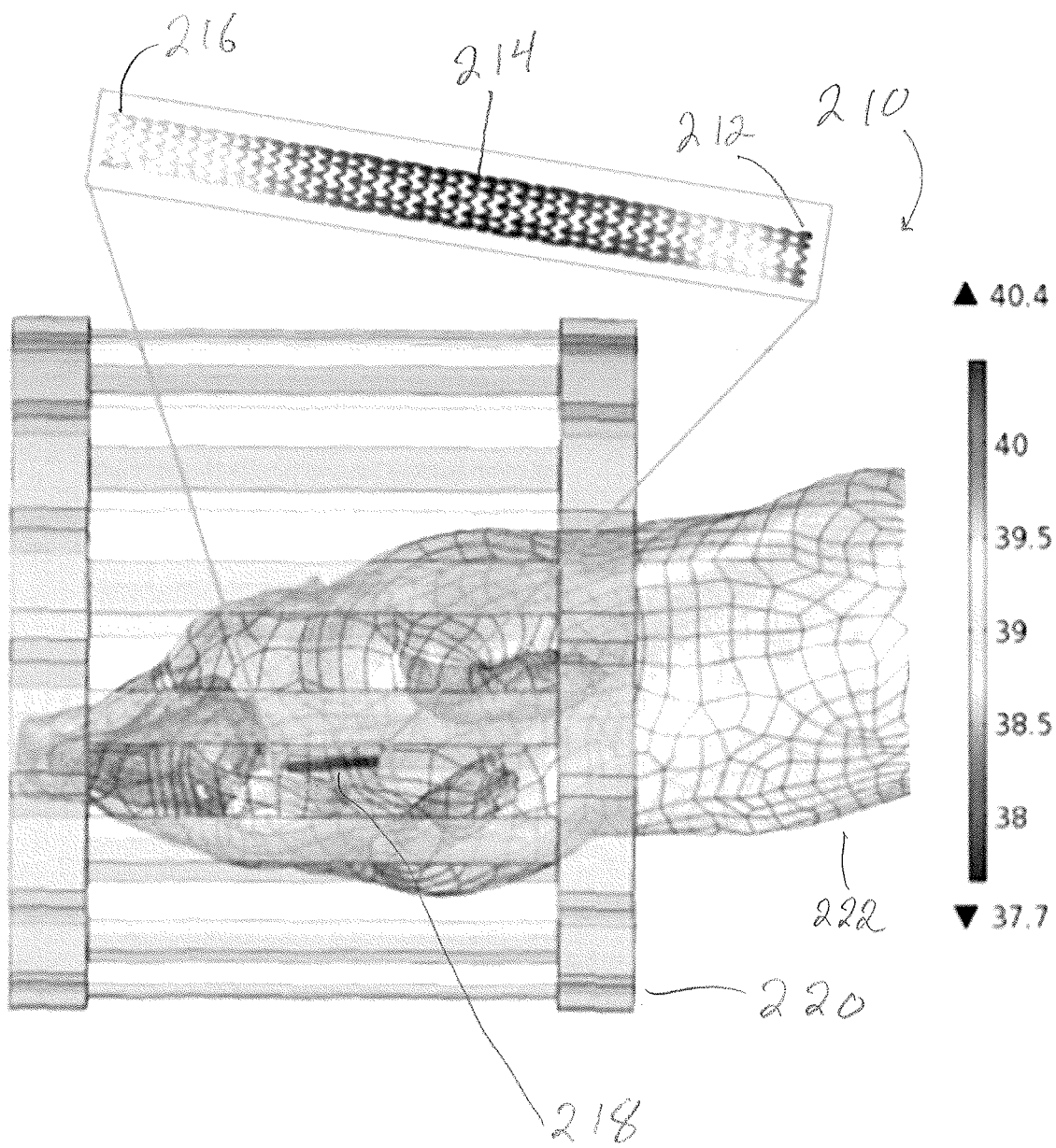
FIG. 5B illustrates an animal with a distal stent located within an MRI scanner.

As is illustrated in FIGS. 4A-5B, to demonstrate application to implanted devices in vivo, the temperature increase associated with a metallic device implanted in a large mammal and subjected to MRI RF scanning was measured and simulated. A virtual pig anatomy 180, 190 was created to demonstrate the ability of the present invention to integrate patient specific body scans into a prediction of the RF. FIGS. 4A and 4B shows the pig body used in the analysis with the internal anatomical features. RF heating was induced using a 3.0 T MRI system with a Whole Body Specific Absorption Rate (WBSAR) of approximately 5.5 W/kg designed to provide maximum heating. A computational simulation of the RF induced heating was performed with the simplified virtual pig anatomy as shown in FIGS. 5A and 5B.

FIG. 5A illustrates experimental and predicted results 200 of a temperature rise of approximately 3° C. for the post-mortem experiments (202) and simulation (204). Specifically, predicted and measured transient temperature history of stent exposed to RF field of MRI, with temperature contour of stent and location in virtual pig anatomy. The in vivo temperature rise (not shown) was less than 1° C., indicating the importance of blood flow and physiological heat transfer mechanisms. The standard MR safety phantom test (ASTM F2182) for this particular device resulted in temperature rises of over 10° C. at 2 W/kg and over 27° C. at 5.5 W/kg. These results demonstrate the inadequacy of the standard phantom testing for predicting in vivo response and the need for the present invention described here.

FIG. 5B illustrates the simulation performed 210. A stent 218 is placed within the animal's body 222, which is placed into an MRI machine 220. The simulation shows that the end points 216 and 212 have relatively significant heating, while the central portion 214 remains relatively cool.

We have demonstrated 1) the ability to accurately simulate RF-induced heating of a lead wire using a priori knowledge of lead configuration, scanner hardware and pulse sequence parameters, and 2) the ability to accurately simulate the RF-induced heating of an implanted metallic device in a large animal model.

In summary, the present invention is a tool that predicts the interaction between the electromagnetic fields of an MRI and implanted devices in vitro and in vivo.

Embodiments or examples, illustrated in the inline drawings are disclosed below using specific language. It will nevertheless be understood that the embodiments or examples are not intended to be limiting. Any alterations and modifications in the disclosed embodiments, and any further applications of the principles disclosed in this document are contemplated as would normally occur to one of ordinary skill in the pertinent art.

Embodiment can employ or involve a computer-readable medium including processor-executable instructions configured to implement one or more embodiments of the techniques presented herein. Many such computer-readable media may be devised by those of ordinary skill in the art that are configured to operate in accordance with the techniques presented herein.

As used in this application, the terms "component", "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, or a computer. By way of illustration, both an application running on a controller and the controller may be a component. One or more components residing within a process or thread of execution and a component may be localized on one computer or distributed between two or more computers.

Further, the claimed subject matter is implemented as a method, apparatus, or article of manufacture using standard programming or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the Example computing devices include, but are not limited to, personal computers, server computers, hand-held or laptop devices, mobile devices, such as mobile phones, Personal Digital Assistants (PDAs), media players, and the like, multiprocessor systems, consumer electronics, mini computers, mainframe computers, distributed computing environments that include any of the above systems or devices, etc.

Generally, embodiments are described in the general context of "computer readable instructions" being executed by one or more computing devices. Computer readable instructions may be distributed via computer readable media as will be discussed below. Computer readable instructions may be implemented as program modules, such as functions, objects, Application Programming Interfaces (APIs), data structures, and the like, that perform one or more tasks or implement one or more abstract data types. Typically, the functionality of the computer readable instructions are combined or distributed as desired in various environments.

Although the subject matter has been described in language specific to structural features or methodological acts, it is to be understood that the subject matter of the appended claims is not necessarily limited to the specific features or acts described above. Rather, the specific features and acts described above are disclosed as example embodiments.

Various operations of embodiments are provided herein. The order in which one or more or all of the operations are described should not be construed as to imply that these operations are necessarily order dependent. Alternative ordering will be appreciated based on this description. Further, not all operations may necessarily be present in each embodiment provided herein.

As used in this application, "or" is intended to mean an inclusive "or" rather than an exclusive "or". Further, an inclusive "or" may include any combination thereof (e.g., A, B, or any combination thereof). In addition, "a" and "an" as used in this application are generally construed to mean "one or more" unless specified otherwise or clear from context to be directed to a singular form. Additionally, at least one of A and B and/or the like generally means A or B or both A and B. Further, to the extent that "includes", "having", "has", "with", or variants thereof are used in either the detailed description or the claims, such terms are intended to be inclusive in a manner similar to the term "comprising".

Although the disclosure has been shown and described with respect to one or more implementations, equivalent alterations and modifications will occur based on a reading and understanding of this specification and the annexed drawings. The disclosure includes all such modifications and alterations and is limited only by the scope of the following claims.

What is claimed:

1. A method of ascertaining temperature impact on tissue of a patient with at least one medical implant from an MRI procedure comprising the steps of:
    a) mapping with an imaging unit location, size and, orientation of a medical implant in a particular patient, and store said location, size and, orientation in a mapped data;
    b) translating the mapped data of the particular patient to a model patient of gender, age, weight, height and body structure of the particular patient with a model medical implant;
    c) determining the parameters of an MRI unit to be used in an MRI procedure of the particular patient; and
    d) computing the temperature profile of the medical implant on exposure of the model patient to the selected MRI procedure to ascertain temperature impact on tissue exposure to the MRI procedure.

2. The method of ascertaining temperature impact on tissue of a patient with at least one medical implant from a MRI procedure as claimed in claim 1, wherein Specific Absorption Rate is considered in computing the temperature profile.

3. The method of ascertaining temperature impact on tissue of a patient with at least one medical implant from an MRI procedure as claimed in claim 1, wherein the medical implant is selected from the group consisting of a pacemaker, vena casa filter, distal stent, pacemaker leads, cardioverter defibrillator, neuro stimulator, and an orthopedic device.

4. The method of ascertaining temperature impact on tissue of a patient with at least one medical implant from an MRI procedure as claimed in claim 1, wherein the medical implant is a tattoo.

5. The method of ascertaining temperature impact on tissue of a patient with at least one medical implant from an MRI procedure as claimed in claim 1, wherein the imaging unit is an X-ray unit.

6. The method of ascertaining temperature impact on tissue of a patient with at least one medical implant from an MRI procedure as claimed in claim 1, wherein the imaging unit is a CT scan unit.

7. A method of ascertaining temperature impact on tissue of a patient with a tattoo and at least one other medical implant from an MRI procedure comprising the steps of:
    a) mapping with an imaging unit location, size and orientation of a medical implant in a particular patient being evaluated for an MRI procedure, and store said location, size and, orientation in a mapped data;
    b) translating the mapped data of the particular patient to a model patient of gender, age, weight, height and body structure of the particular patient with a model medical implant,
    c) determining the parameters of an MRI unit to be used in an MRI procedure of the particular patient; and
    d) computing a temperature profile in tissue of the model patient on exposure of the particular patient with the MRI unit by the selected MRI procedure.

8. The method of ascertaining temperature impact on tissue of a patient with a tattoo and at least one other medical implant from a MRI procedure as claimed in claim 7, wherein Specific Absorption Rate is considered in computing the temperature profile.

9. The method of ascertaining temperature impact on tissue of a patient with a tattoo and at least one other medical implant from a MRI procedure as claimed in claim 7, wherein the medical implant is selected from the group consisting of a pacemaker, vena casa filter, distal stent, pacemaker leads, cardioverter defibrillator, neuro stimulator, and an orthopedic device.

10. The method of ascertaining temperature impact on tissue of a patient with a tattoo and at least one other medical implant from a MRI procedure as claimed in claim 7, wherein the imaging unit is a CT Scan unit.

* * * * *